US012782246B2

United States Patent
(12) United States Patent
Miyauchi et al.

(10) Patent No.: US 12,782,246 B2
(45) Date of Patent: Nov. 3, 2026

(54) WATER SAMPLING METHOD, WATER SAMPLING DEVICE, AND WATER SAMPLING SYSTEM

(71) Applicant: Yokogawa Electric Corporation, Musashino (JP)

(72) Inventors: Yuki Miyauchi, Musashino (JP); Tomoyuki Taguchi, Musashino (JP); Hiroyuki Katayama, Tokyo (JP)

(73) Assignee: Yokogawa Electric Corporation, Musashino (JP)

( * ) Notice: Subject to any disclaimer, the term of this patent is extended or adjusted under 35 U.S.C. 154(b) by 500 days.

(21) Appl. No.: 18/283,122

(22) PCT Filed: Feb. 2, 2022

(86) PCT No.: PCT/JP2022/004132
§ 371 (c)(1),
(2) Date: Sep. 20, 2023

(87) PCT Pub. No.: WO2022/201889
PCT Pub. Date: Sep. 29, 2022

(65) Prior Publication Data
US 2024/0167918 A1 May 23, 2024

(30) Foreign Application Priority Data
Mar. 26, 2021 (JP) ................................ 2021-054183

(51) Int. Cl.
*G01N 1/00* (2006.01)
*G01N 1/10* (2006.01)
*G01N 33/18* (2006.01)

(52) U.S. Cl.
CPC .......... *G01N 1/10* (2013.01); *G01N 33/1866* (2013.01)

(58) Field of Classification Search
CPC .................... C02F 2209/11; G01N 2001/1031
See application file for complete search history.

(56) References Cited

U.S. PATENT DOCUMENTS

2008/0289402 A1 11/2008 Chowdhury
2016/0340204 A1 11/2016 Chowdhury et al.
2020/0109063 A1* 4/2020 Nakajima .............. C02F 1/686

FOREIGN PATENT DOCUMENTS

CN 102073292 A 5/2011
FR 3053359 A1 * 1/2018 .............. C12Q 1/04
(Continued)

OTHER PUBLICATIONS

European Search Report dated Sep. 9, 2025, issued in counterpart EP Application No. 22774691.4. (9 pages).
(Continued)

*Primary Examiner* — Nathan A Bowers
(74) *Attorney, Agent, or Firm* — WHDA, LLP

(57) ABSTRACT

A water sampling method including: a detection step of detecting an index value related to an amount of microorganisms in a liquid flowing through a flow channel; a determination step of determining whether the index value detected in the detection step has reached a threshold value; and a water sampling step of, when determining in the determination step that the index value has reached the threshold value, sampling via a water sampling flow channel the liquid flowing through the flow channel as a liquid sample to be used for measurement of the microorganisms.

11 Claims, 8 Drawing Sheets

100

(56) References Cited

FOREIGN PATENT DOCUMENTS

| | | | | |
|---|---|---|---|---|
| GB | 2514609 | A | * 12/2014 | .............. C12Q 1/04 |
| JP | 2007-263892 | A | 10/2007 | |
| JP | 2007-263893 | A | 10/2007 | |
| JP | 2008-26257 | A | 2/2008 | |
| JP | 2017-070231 | A | 4/2017 | |
| WO | 2011/061310 | A1 | 5/2011 | |
| WO | WO-2015115995 | A1 | * 8/2015 | ............. C02F 1/008 |

OTHER PUBLICATIONS

Extended (Supplementary) European Search Report dated Jan. 30, 2025, issued in EP Application No. 22774691.4. (66 pages).

Inoue et al., "Spatial and temporal profiles of enteric viruses in the coastal waters of Tokyo Bay during and after a series of rainfall events", Science of The Total Environment, Jul. 20, 2020, vol. 727, 138502. (4 pages).

Katayama et al., "Development of a Virus Concentration Method and Its Application to Detection of Enterovirus and Norwalk Virus from Coastal Seawater", Applied and Environmental Microbiology, Mar. 2002, vol. 68, No. 3, pp. 1033-1039. (7 pages).

Office Action dated May 9, 2026, issued in counterpart CN Application No. 202280024002.7, with English translation. (15 pages).

* cited by examiner

100

100

WATER SAMPLING METHOD, WATER SAMPLING DEVICE, AND WATER SAMPLING SYSTEM

CROSS-REFERENCE TO RELATED APPLICATION

The present application claims priority to and the benefit of Japanese Patent Application No. 2021-054183 filed Mar. 26, 2021, the entire contents of which are incorporated herein by reference.

TECHNICAL FIELD

The present disclosure relates to a water sampling method, a water sampling device, and a water sampling system.

BACKGROUND

Technologies are known that are related to water sampling of a liquid for the purposes of managing the water quality of treated water in water treatment infrastructure and inspecting the water quality of water bodies such as oceans. For example, Non-Patent Literature (NPL) 1 describes a method of continuously sampling water by allowing a sampling tube to reach a desired location or depth and driving a suction pump, the method being useful when a volume of liquid is needed that cannot be sampled at once using a typical water sampler, such as a Van Dorn sampler, a Niskin sampler, and the like. For example, NPL 2 describes a negatively charged membrane method, which uses a negatively charged membrane to collect microorganisms from water.

CITATION LIST

Non-Patent Literature

NPL 1: Inoue et al, "Spatial and temporal profiles of enteric viruses in the coastal waters of Tokyo Bay during and after a series of rainfall events", Science of The Total Environment, July 2020, Vol. 727, 138502

NPL 2: Katayama et al, "Development of a Virus Concentration Method and Its Application to Detection of Enterovirus and Norwalk Virus from Coastal Seawater", Applied and Environmental Microbiology, March 2002, Vol. 68, No. 3, p. 1033-1039

SUMMARY

A water sampling method according to at least one embodiment comprises: a detection step of detecting an index value related to an amount of microorganisms in a liquid flowing through a flow channel; a determination step of determining whether the index value detected in the detection step has reached a threshold value; and a water sampling step of, when determining in the determination step that the index value has reached the threshold value, sampling via a water sampling flow channel the liquid flowing through the flow channel as a liquid sample to be used for measurement of the microorganisms.

A water sampling device according to at least one embodiment comprises: a sensor configured to detect an index value related to an amount of microorganisms in a liquid flowing through a flow channel; a calculator configured to determine whether the index value detected by the sensor has reached a threshold value; and a controller configured to, when the calculator determines that the index value has reached the threshold value, control a water sampling flow channel so that the liquid flowing through the flow channel is sampled as a liquid sample to be used for measurement of the microorganisms.

DETAILED DESCRIPTION

Figure 1:
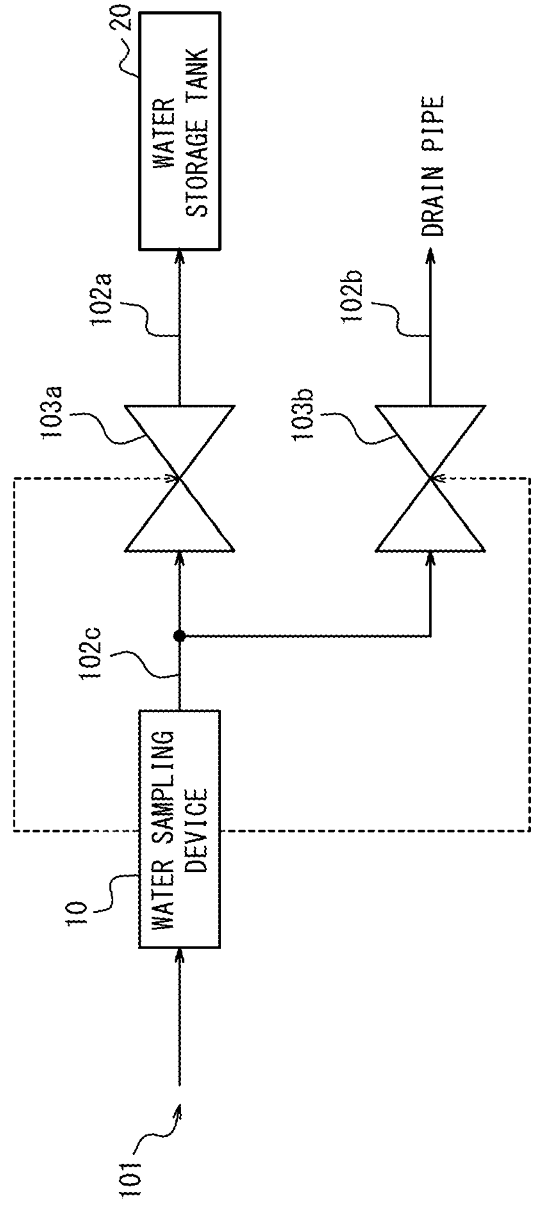
FIG. 1 is a schematic diagram of a water sampling system according to a first embodiment of the present disclosure.

Water treatment systems need information on how much control performance is achievable for a defined microbial load. However, the conventional technology described in NPL 1, for example, focuses on how quickly liquid may be sampled in a short period of time. In the conventional technology described in NPL 1 and 2, sufficient consideration was not given to sampling of liquid at a time when a liquid sample that includes a defined microbial load is thoroughly and appropriately obtainable. It would be helpful to provide a water sampling method, a water sampling device, and a water sampling system able to obtain a liquid sample including a defined microbial load at an appropriate time. According to the present disclosure, the water sampling method, the water sampling device, and the water sampling system are provided that are able to obtain a liquid sample including a defined microbial load at an appropriate time.

A water sampling method according to at least one embodiment comprises: a detection step of detecting an index value related to an amount of microorganisms in a liquid flowing through a flow channel; a determination step of determining whether the index value detected in the detection step has reached a threshold value; and a water sampling step of, when determining in the determination step that the index value has reached the threshold value, sampling via a water sampling flow channel the liquid flowing through the flow channel as a liquid sample to be used for measurement of the microorganisms.

Accordingly, a liquid sample including a defined microbial load is obtainable at an appropriate time. Sampling of liquid is possible at a time when a liquid sample including a defined microbial load is thoroughly and appropriately obtainable. Therefore, contribution may be made to a proper understanding of water quality fluctuation in a liquid where the index value reaches the threshold value. For example, by sampling liquid as a liquid sample used to measure microorganisms when the index value has reached the threshold value, a water sampling process may be appropriately executed when the index value reaches the threshold value.

According to an embodiment, the water sampling method further comprises a water storage step of storing the liquid sampled in the water sampling step in a water storage tank. Accordingly, the liquid sampled via the water sampling flow channel may be stored over a defined period of time.

According to an embodiment, the water sampling method further comprises a collection step of collecting, by a filter, the microorganisms in the liquid sampled in the sampling step. Accordingly, more convenient evaluation of microbial load becomes possible in subsequent measurement of microorganisms.

According to an embodiment, the water sampling method further comprises a concentration step of concentrating the microorganisms collected by the filter in the collection step to purify a concentrate. Accordingly, a microbial load indicator may be directly collected by the filter to concentrate the microorganisms. Therefore, even a liquid sample that would be below a detection limit before concentration may be a liquid sample that is possible to evaluate in subsequent microorganism measurement.

A water sampling device according to at least one embodiment comprises: a sensor configured to detect an index value related to an amount of microorganisms in a liquid flowing through a flow channel; a calculator configured to determine whether the index value detected by the sensor has reached a threshold value; and a controller configured to, when the calculator determines that the index value has reached the threshold value, control a water sampling flow channel so that the liquid flowing through the flow channel is sampled as a liquid sample to be used for measurement of the microorganisms.

Accordingly, a liquid sample including a defined microbial load is obtainable at an appropriate time. The water sampling device is capable of sampling liquid at a time when a liquid sample including a defined microbial load is thoroughly and appropriately obtainable. Thus, the water sampling device may contribute to a proper understanding of water quality fluctuation in a liquid where the index value reaches the threshold value. For example, by sampling liquid as a liquid sample used to measure microorganisms when the calculator determines that the index value has reached the threshold value, the water sampling device may appropriately execute a water sampling process when the index value reaches the threshold value.

A water sampling system according to at least one embodiment comprises: the water sampling device described above; and the water sampling flow channel through which the liquid to be sampled as the liquid sample flows.

Accordingly, a liquid sample including a defined microbial load is obtainable at an appropriate time. The water sampling system is capable of sampling liquid at a time when a liquid sample including a defined microbial load is thoroughly and appropriately obtainable. Thus, the water sampling system may contribute to a proper understanding of water quality fluctuation in a liquid where the index value reaches the threshold value. For example, by sampling liquid as a liquid sample used to measure microorganisms when the calculator determines that the index value has reached the threshold value, the water sampling system may appropriately execute a water sampling process when the index value reaches the threshold value.

According to an embodiment, the water sampling system further comprises a water storage tank configured to store the liquid sampled based on the control of the water sampling flow channel by the controller. Accordingly, the water sampling system is able to store the liquid sampled over a defined period of time, based on the control of the water sampling flow channel by the controller of the water sampling device.

According to an embodiment, the water sampling system further comprises a filter configured to collect the microorganisms in the liquid sampled based on the control of the water sampling flow channel by the controller. Accordingly, more convenient evaluation of microbial load becomes possible in subsequent measurement of microorganisms.

According to an embodiment, the water sampling system further comprises a concentration device configured to concentrate the microorganisms collected by the filter to purify a concentrate. Accordingly, the water sampling system is able to directly collect a microbial load indicator by the filter to concentrate the microorganisms. Therefore, the water sampling system may use even a liquid sample that would be below a detection limit before concentration as a liquid sample that is possible to evaluate in subsequent microorganism measurement.

Background technology and problems are described in more detail.

For example, NPL 1 also describes that when a large volume of liquid sampled cannot be stored in a sampling container, target viruses, particles, and the like, are collected by adsorption onto a negatively charged membrane, and permeated liquid is drained onsite.

In addition to the conventional technologies described in NPL 1 as above, the following technologies related to liquid water sampling are also known; for example.

For example, the Van Dorn sampler and Niskin sampler are known as typical water samplers for sampling liquids. Such a typical water sampler is attached to the end of a rope and sunk to a desired depth in a body of water such as a swimming pool, ocean, river, and the like. A typical water sampler closes caps as a messenger weight drops along the rope to the sampler. A typical water sampler collects a sample at a specific time at a point or depth from which a liquid sample is to be collected.

As an example of an autosampler for water sampling, an automatic water sampler capable of sampling from a few mL to 10 L of liquid at programmed times is also known. Such autosamplers are implemented in automatic water samplers managed by timer controls or other means to ascertain a moment of water quality. For example, an autosampler flows liquid through a pipe or hose connected to a water sampling point to a water quality analyzer, which will periodically sample several mL to several L of water on an hourly, daily, weekly, monthly, etc. basis.

Water treatment systems need information on how much control performance is achievable for a worst or maximum microbial load, for example. However, none of the above conventional technologies adequately considered sampling of liquid at a time when a liquid sample including a worst or maximum microbial load is thoroughly and appropriately obtainable.

For example, in the conventional technology described in NPL 1, water sampling is limited to specific timing within a few seconds to a few tens of minutes. Therefore, an analyzable range of water quality of treated water or a body of water is limited to that at the time of water sampling. The liquid sampled is not a representative sample fit for the purpose of ascertaining the water quality of the liquid including the worst or maximum microbial load in a water treatment system. In particular, river water, sewage, and the like are susceptible to runoff loads from watersheds, including industrial and domestic wastewater, and to weather conditions. Therefore, momentary water sampling limited to the point of sampling likely does not reflect the actual water quality of the liquid that includes the worst or maximum microbial load.

Such problems apply equally to the typical water sampler and autosampler described above. In a water sampling method using a typical water sampler, water is sampled at a specific time and the liquid sample may only be analyzed as a momentary snapshot at the time of the sampling. Similarly, in the water sampling method using an autosampler, water is sampled at a specific time set by a timer, and the liquid sample may only be analyzed as a momentary snapshot at the time of the water sampling. The intermittent water sampling described above also likely does not adequately monitor increases and decreases in microbial load and likely does not reflect the actual water quality of the liquid that includes the worst or maximum microbial load.

Therefore, liquid sampled using conventional technology is not a representative sample fit for the purpose of managing the water quality of treated water in a water treatment system or the purpose of ascertaining control performance. When a liquid sample including the worst or maximum microbial load cannot be recovered, quantitative information on the maximum load cannot be obtained and, for example, important information on the maximum load relative to an upper limit of control performance of the water treatment system will be omitted. On the other hand, performing water sampling continuously for long periods of time or intermittently at high frequency places a heavy burden on a person sampling water.

The following describes a water sampling device 10, a water sampling system 100, and a water sampling method able to solve these problems.

The water sampling device 10, the water sampling system 100, and the water sampling method described below are applicable to a wide variety of fields and uses. For example, these may be used to sample water to ascertain water quality management and treatment performance in water treatment infrastructure, including water purification plants, sewage treatment plants, water reclamation facilities, seawater desalination facilities, and the like. In such cases, particulates, colloidal dispersions, microorganisms, and the like that have a negative charge and are suspended in liquid that is sampled may be efficiently collected by a filter.

For example, the water sampling device 10, the water sampling system 100, and the water sampling method may be used for water sampling to ascertain the treatment performance of a water treatment system. Water treatment systems include coagulation tanks, sedimentation tanks, sand filtration, microfiltration membranes, ultrafiltration membranes, reverse osmosis membranes, ozone contact tanks, activated carbon filtration tanks, ultraviolet (UV) irradiation tanks, disinfection tanks using a chlorinating agent, and the like that make up water treatment infrastructure.

For example, the water sampling device 10, the water sampling system 100, and the water sampling method may be applied to the sampling of liquids for inspecting water quality regarding particulates, colloidal dispersions, microorganisms, and the like, to ascertain dynamics in environmental studies of rivers, oceans, water features, and the like.

For example, the water sampling device 10, the water sampling system 100, and the water sampling method may be applied to the sampling of liquids for inspecting water quality regarding particulates, colloidal dispersions, microorganisms, and the like, to ascertain the risk of microbial infection in cities including water bodies and environmental infrastructure.

For example, the water sampling device 10, the water sampling system 100, and the water sampling method may be applied to the sampling of liquids for inspecting water quality regarding particulates, colloidal dispersions, microorganisms, and the like for purposes such as qualitative risk, safety monitoring, and quality control of liquids used for beverages or in the production of processed food, to quantify risk or to verify against a threshold value to determine safety.

For example, the water sampling device 10, the water sampling system 100, and the water sampling method may be applied to the sampling of liquids for quality control inspection, such as in the manufacture of pharmaceutical products.

As used herein, "microorganisms" as a subject of microbial load include, for example, protozoa, bacteria, viruses, and the like. "Protozoa" include, for example, *Cryptosporidium, Giardia*, and the like. "Bacteria" include, for example, *Escherichia coli, Staphylococcus, Vibrio cholerae, Mycobacterium tuberculosis, Helicobacter pylori*, and the like. "Viruses" include, for example, norovirus, adenovirus, enteric viruses, pepper mild mottle virus (PMMoV), and the like.

Embodiments of the present disclosure are described below with reference to the drawings.

First Embodiment

FIG. 1 is a schematic diagram of the water sampling system 100 according to a first embodiment of the present disclosure. Configuration and functions of the water sampling system 100 according to the first embodiment are described with reference to FIG. 1. In FIG. 1, solid arrows connecting components indicate liquid flow. Dashed arrows starting from the water sampling device 10 indicate flow of signals.

The water sampling system 100 is a system used to sample and store as a liquid sample a liquid such as treated water in water treatment infrastructure. The liquid that is sampled as a liquid sample by the water sampling system 100 flows in one direction through, for example, piping that forms part of the water treatment infrastructure. For example, assume the water quality of such a liquid varies over time. The piping may constitute a main flow channel in the water treatment infrastructure or a bypass flow channel branched off from the main flow channel.

The water sampling system 100 has a water sampling port 101. The water sampling port 101 includes, for example, a removable valve that is attached to a side of the piping described above that forms part of the water treatment infrastructure. A portion of the liquid flowing in one direction through such piping is sampled by the water sampling system 100 using the location of the valve in the piping as a sampling point.

The water sampling system 100 has the water sampling device 10 that controls a water sampling process in the water sampling system 100. The water sampling device 10 is disposed downstream of the water sampling port 101. The water sampling system 100 has a water storage tank 20 that is disposed downstream from the water sampling device 10. The water sampling system 100 has a water sampling flow channel 102*a* and a drainage flow channel 102*b* where liquid flow branches into two between the water sampling device 10 and the water storage tank 20. The water sampling system 100 has a flow channel 102*c* disposed between the water sampling port 101 and the point of branching to the water sampling flow channel 102*a* and the drainage flow channel 102*b*. The water sampling device 10 is disposed on the flow channel 102*c*. The water sampling system 100 has a first solenoid valve 103*a* disposed between the water sampling device 10 and the water storage tank 20 in the water sampling flow channel 102*a* and a second solenoid valve 103*b* disposed in the drainage flow channel 102*b*.

When the first solenoid valve 103*a* is open and the second solenoid valve 103*b* is closed, liquid entering the water sampling system 100 from the water sampling port 101 flows through the flow channel 102*c* and then through the water sampling flow channel 102*a* into the water storage tank 20. The water storage tank 20 is disposed at the end of the water sampling flow channel 102*a* opposite the water sampling port 101 and stores liquid that flows through the water sampling flow channel 102*a*. When the first solenoid valve 103*a* is closed and the second solenoid valve 103*b* is open, liquid entering the water sampling system 100 from the water sampling port 101 flows through the flow channel 102*c* and then through the drainage flow channel 102*b* to a drain pipe.

When liquid flows from the water sampling port 101 through each flow channel as illustrated in FIG. 1, turbidity, precipitate, and the like in the liquid may block pipes that make up each flow channel. To suppress the occurrence of such blockages in the piping, the pipes constituting each flow channel may be designed so that flow velocity of the liquid flowing through is 1 m/s or more. For example, when the inner diameter of the pipes constituting each flow channel is 15 mm, a flow rate corresponding to the flow velocity of 1 m/s is about 170 mL/s (about 10 L/min).

Figure 2:
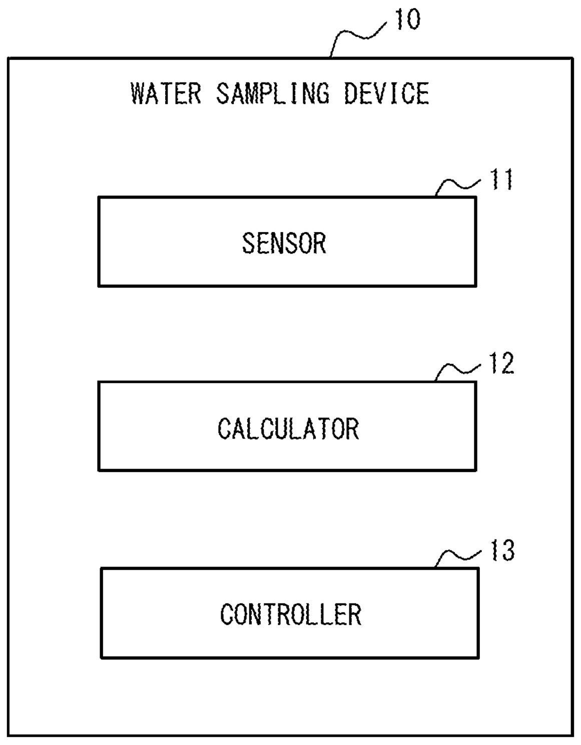
FIG. 2 is a functional block diagram illustrating a schematic configuration of a water sampling device illustrated in FIG. 1.

FIG. 2 is a functional block diagram illustrating a schematic configuration of the water sampling device 10 illustrated in FIG. 1. Configuration and functions of the water sampling device 10 illustrated in FIG. 1 are described with reference to FIG. 2. The water sampling device 10 has a sensor 11, a calculator 12, and a controller 13.

The sensor 11 includes any sensor element, sensor module, or sensor device that detects an index value related to the amount of microorganisms in liquid flowing through the flow channel. For example, the sensor 11 is disposed on the flow channel 102*c* illustrated in FIG. 1 and detects an index value related to the amount of microorganisms in the liquid that enters the water sampling system 100 from the water sampling port 101. The sensor 11 outputs the detected index value as a detection signal to the calculator 12.

As used herein, "index value" includes, for example, flow cytometer particles, turbidity, chromaticity, chemical oxygen demand (COD), biochemical oxygen demand (BOD), total organic carbon (TOC), dissolved oxygen (DO), suspended solids (SS), chlorophyll concentration, total nitrogen (T-N), total phosphorus (T-P), organic pollutant concentration (UV absorption analysis), adenosine triphosphate (ATP), enzyme activity, and the like.

For example, when the index value includes flow cytometer particles, the sensor 11 includes a flow imaging device. For example, when the index value includes turbidity, the sensor 11 includes a nephelometric turbidity sensor, a light absorption sensor, and the like. For example, when the index value includes chromaticity, the sensor 11 includes a transmitted light chromaticity meter. For example, when the index value includes COD, the sensor 11 includes a COD analyzer. For example, when the index value includes BOD, the sensor 11 includes a BOD meter, a biosensor-type rapid BOD meter, and the like.

For example, when the index value includes TOC, the sensor 11 includes a TOC meter. For example, when the index value includes DO, the sensor 11 includes an optical DO meter. For example, when the index value includes SS, the sensor 11 includes a backscattered light or transmitted light SS sensor. For example, when the index value includes chlorophyll concentration, the sensor 11 includes a chlorophyll fluorescence sensor. For example, when the index value includes T-N, the sensor 11 includes devices based on an ultraviolet method, a hydrazine sulfate reduction method, a copper-cadmium reduction method, and the like, as well as automatic quantification devices and the like.

For example, when the index value includes T-P, the sensor 11 includes devices based on a heat concentration method, a solvent extraction method, and the like, as well as automatic quantification devices and the like. For example, when the index value includes organic pollutant concentration (ultraviolet absorption analysis), the sensor 11 includes a UV meter. For example, when the index value includes ATP, the sensor 11 includes an ATP meter. For example, when the index value includes enzyme activity, the sensor 11 includes an enzyme substrate fluorescence sensor, a colorimetric sensor, a light sensor, and the like.

The calculator 12 determines whether the index value detected by the sensor 11 has reached a threshold value. The calculator 12 includes any calculator element or calculation module capable of performing such a determination process. The calculator 12 may, for example, set different threshold values for comparison with the index value detected by the sensor 11 for each treatment facility of the water treatment infrastructure.

For example, in the case of an existing treatment facility, the correlation between microbial load and a reference value of the index value obtained during the operation of the system may be calculated, and the index value with the highest correlation may be selected as the threshold value. For example, in the case of an existing treatment facility, the average value of variation within a day, daily variation, weekly variation, monthly variation, seasonal variation, and the like may be calculated in advance from the index value obtained during the operation of the system, and the threshold value may be set from a value of variation from the average value.

For the value of variation, the average value and standard deviation $\sigma$ of variation within a day, daily variation, weekly variation, monthly variation, seasonal variation, and the like may be calculated in advance from the index value obtained during the operation of the system, a confidence interval for the average value may be set from the standard deviation, and a value exceeding the confidence interval may be regarded as having a significant difference and set as the threshold value. For the value of variation, the average value and standard deviation $\sigma$ of variation within a day, daily variation, weekly variation, monthly variation, seasonal variation, and the like may be calculated in advance from a logarithm of the index value obtained during the operation of the system, a confidence interval for the average value may be set from the standard deviation, and a value exceeding the confidence interval may be regarded as having a significant difference and set as the threshold value.

The confidence interval may be set arbitrarily, but when a value outside 95% of the average value is considered an outlier, the confidence interval is set based on the average value plus 1.96 $\sigma$. When a value outside 99% of the average value is considered an outlier, the confidence interval is set based on the average value plus 2.33 σ.

The threshold value may be set from an empirical value indicating a high value for an environmental factor such as rainfall conditions without being set as a confidence interval. The above value of variation may be incorporated into machine learning or the like so that the index value obtained while the system is in operation is always fed back into calculation of the threshold value. The threshold value need not be a threshold value for a single index value, and may be based on results obtained from multivariate analysis, such as principal component regression analysis and classification of a plurality of index values, neural networks, machine learning, and the like. Also in this case, data may be constantly fed back into the calculation of the threshold value.

Microbial contamination of viruses, for example, does not necessarily exhibit a linear correlation with the index value. Unless microbial contamination is relatively high when an index value such as turbidity is high, very small viruses and the like from an optical point of view do not exhibit a linear correlation with index values such as turbidity and TOC. Even in such a case, trends may be ascertained based on machine learning results for multiple index values, including non-linearity specific to water sampling locations such as land and water treatment systems. Because trends, including non-linearity, are specific to the water sampling location, the water sampling device 10 may empirically adapt the water sampling method to the water sampling location while performing machine learning.

Otherwise, the threshold value may be set using a statistical method of outlier detection, including the Smirnov-Grubbs test for testing outliers, the use of interquartile ranges, and the like.

The controller 13 includes at least one processor. According to the present embodiment, a "processor" may be, but is not limited to, a general-purpose processor or a dedicated processor specialized for particular processing. The controller 13 is communicatively connected to each component of the water sampling device 10 and controls the overall operation of the water sampling device 10. When the calculator 12 determines that the index value has reached the threshold value, the controller 13 samples water from the liquid used to measure microorganisms. More specifically, the controller 13 controls the water sampling flow channel 102*a* so that the liquid flowing in the flow channel 102*c* is sampled as a liquid sample used to measure microorganisms.

More specifically, when the calculator 12 determines that the index value has reached the threshold value, the controller 13 obtains an output signal from the calculator 12 regarding the determination result. When obtaining such an output signal from the calculator 12, the controller 13 controls the water sampling flow channel 102*a* so that the liquid used to measure microorganisms flows through the water sampling flow channel 102*a* and into the water storage tank 20.

For example, referring to FIG. 1, the two solenoid valves, the first solenoid valve 103*a* and the second solenoid valve 103*b*, are closed in advance. Upon obtaining an output signal from the calculator 12 regarding a determination result that the calculator 12 has determined that the index value has not reached the threshold value, the controller 13 outputs a control signal to the second solenoid valve 103*b* to open the second solenoid valve 103*b*. Accordingly, the first solenoid valve 103*a* remains closed and the second solenoid valve 103*b* opens. In this state, upon obtaining an output signal from the calculator 12 regarding a determination result that the calculator 12 has determined that the index value has reached the threshold value, the controller 13 outputs a control signal to the first solenoid valve 103*a* to open and to the second solenoid valve 103*b* to close. Accordingly, the second solenoid valve 103*b* transitions from open to closed, and the first solenoid valve 103*a* transitions from closed to open. At this time, the water storage tank 20 stores the liquid sampled via the water sampling flow channel 102*a* based on the control of the water sampling flow channel 102*a* by the controller 13.

The water sampling device 10 may perform constant monitoring in real time or continuous monitoring according to a measurement interval of several minutes to several hours by the sensor 11. The calculator 12 of the water sampling device 10 may use such continuous monitoring to determine whether or not the liquid needs to be sampled into the water storage tank 20 based on a comparison of the index value to the threshold value. The water sampling device 10 may control the water sampling flow channel 102*a* so that a sampling volume ranging from a few mL to 1000 L is achieved upon a determination that water sampling of liquid into the water storage tank 20 is necessary.

The sampled liquid is measured as a liquid sample by any measuring device capable of measuring microorganisms in the liquid. More specifically, the sampled liquid may be used to detect microorganisms in the liquid and for other qualitative or quantitative measurements. Methods used for detection of microorganisms and other qualitative and quantitative measurements include culture methods, ATP measurement, catalase measurement, CO2 measurement, matrix-assisted laser desorption/ionization time-of-flight mass spectrometry (MALDI-TOF MS), quantitative polymerase chain reaction (qPCR), loop-mediated isothermal amplification (LAMP) methods, deoxyribonucleic acid (DNA) base sequence analysis, DNA microarray methods, immunochromatography methods, capillary electrophoresis, staining methods, fluorescence methods, enzymatic methods, electrical impedance methods, microcolony detection methods, and the like.

The measuring device may perform a method such as a labeled antibody method. The measuring device may, for example, perform fluorescence in situ hybridization (FISH), a fluorometric measurement of the expression of a specific chromosome or gene in a tissue or cell using a fluorescent substance. The measuring device may perform a method such as fluorescence immunoassay (FIA) methods that measure antigen-antibody reactions using a fluorescent substance such as europium as a label, indirect fluorescent antibody (IFA) methods that measure reactions of serum (antibody) labeled with a fluorescent substance, such as a pathogen as an antigen, enzyme-linked immunosorbent assay (ELISA) methods, latex agglutination methods, antibody titration, and the like.

Figure 3:
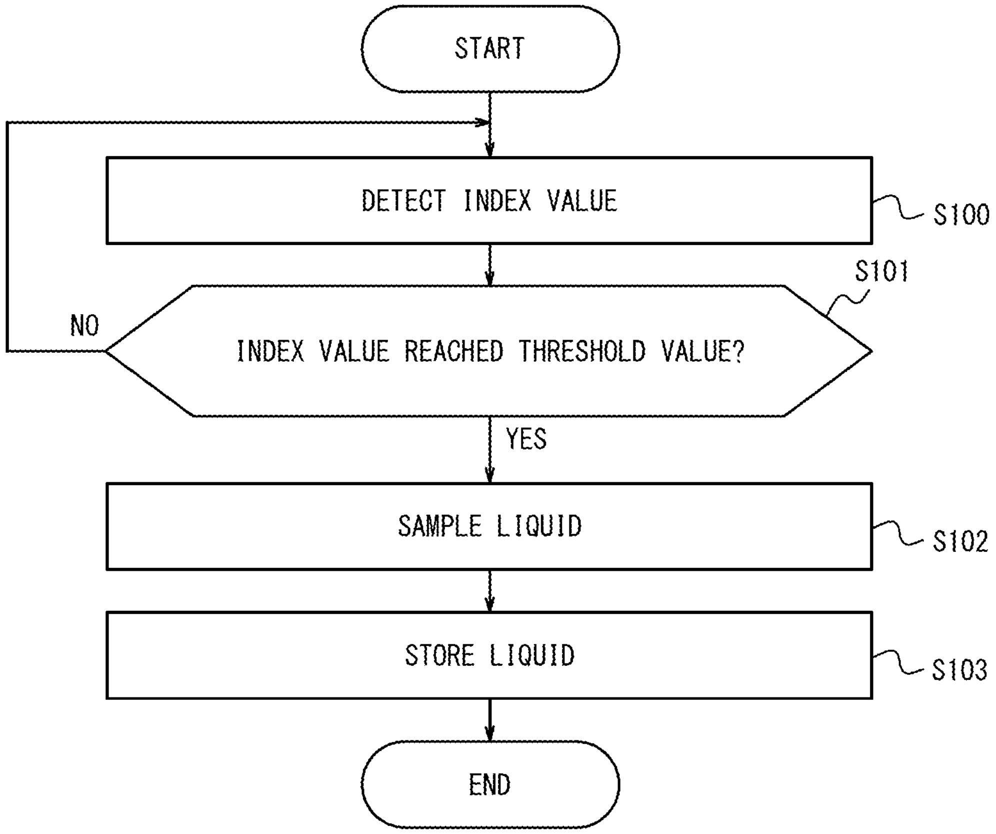
FIG. 3 is a flowchart for explaining a water sampling method executed by the water sampling system illustrated in FIG. 1.

FIG. 3 is a flowchart for explaining the water sampling method performed by the water sampling system 100 illustrated in FIG. 1. The water sampling method performed by the water sampling system 100 illustrated in FIG. 1 is described with reference to FIG. 3.

In step S100, the water sampling system 100 detects an index value related to the amount of microorganisms in the liquid flowing through the flow channel 102*c*.

In step S101, the water sampling system 100 determines whether the index value detected in the detection step of step 100 has reached the threshold value. Upon determining that the index value has reached the threshold value, the water sampling system 100 performs step S102. Upon determining that the index value has not reached the threshold value, the water sampling system 100 performs step S100 again.

In step S102, when the water sampling system 100 determines that the index value has reached the threshold value in the determination step of step S101, the liquid flowing in the flow channel 102c is sampled via the water sampling flow channel 102a as a liquid sample used to measure microorganisms. More specifically, the water sampling device 10 of the water sampling system 100 controls the water sampling flow channel 102a so that the liquid flowing in the flow channel 102c is sampled as a liquid sample used to measure microorganisms.

In step S103, the water sampling system 100 stores the liquid sampled in the water sampling step of step S102 in the water storage tank 20.

According to the first embodiment described above, a liquid sample including a defined microbial load is obtainable at an appropriate time. The water sampling device 10 and the water sampling system 100 are capable of sampling liquid at a time when a liquid sample including a defined microbial load is thoroughly and appropriately obtainable. Accordingly, the water sampling device 10 and the water sampling system 100 may contribute to a proper understanding of water quality fluctuation in a liquid where the index value reaches the threshold value. For example, by sampling liquid as a liquid sample used to measure microorganisms when the calculator 12 determines that the index value has reached the threshold value, the water sampling device 10 and the water sampling system 100 may appropriately execute a water sampling process when the index value reaches the threshold value.

Thus, the water sampling device 10 and the water sampling system are capable of thoroughly and appropriately collecting a liquid sample including a worst or maximum microbial load. According to the water sampling method using the water sampling device 10 and the water sampling system 100, detection of sudden fluctuations in water quality is possible and detection of worst-case conditions is possible. Worst-case conditions of water quality at the time of water sampling are reflected in the liquid sample, making it possible to not miss qualitative risks caused by the worst-case conditions. The water sampling device 10 and the water sampling system 100 allow water sampling to evaluate qualitative risk posed by the worst-case conditions at the point of water flow. The water sampling device 10 and the water sampling system 100 are able to collect liquid as a representative sample that reflects the contamination status of the target liquid.

As a result, the water sampling device 10 and the water sampling system 100 are able to collect a representative sample fit for the purpose of managing the water quality of treated water in a water treatment system or the purpose of ascertaining control performance. The water sampling device 10 and the water sampling system 100 are capable of collecting a liquid sample including a worst or maximum microbial load and obtaining quantitative information on the maximum load. For example, the water sampling device 10 and the water sampling system 100 are able to thoroughly obtain important information about the maximum load relative to an upper limit of control performance of the water treatment system. As described above, appropriately ascertaining fluctuations in water quality of liquid and control performance of a water treatment system becomes easy.

In addition, according to the water sampling device 10 and the water sampling system 100, a person sampling water does not need to perform continuous water sampling for long periods of time or intermittent water sampling at high frequency. The automation of water sampling by the water sampling device 10 and the water sampling system 100 reduces the burden related to time constraints on a person sampling water.

The water sampling system 100 having the water storage tank 20 allows the water sampling system 100 to store the liquid sampled via the water sampling flow channel 102a for a defined time, based on the control of the water sampling flow channel 102a by the controller 13 of the water sampling device 10.

Figure 4:
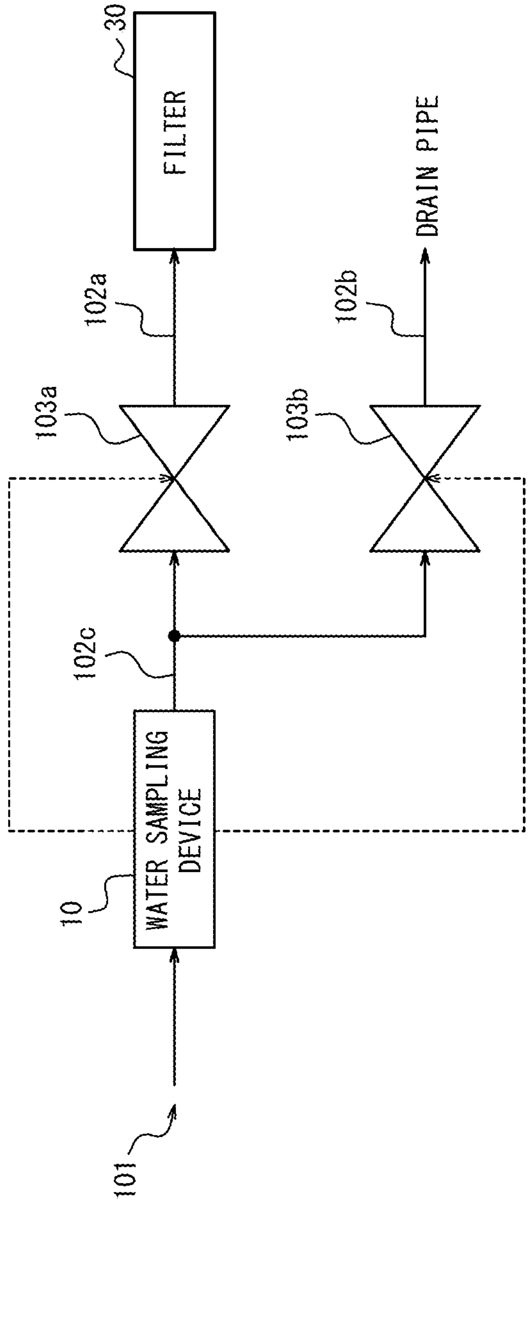
FIG. 4 is a schematic diagram illustrating a first variation of the water sampling system illustrated in FIG. 1.

FIG. 4 is a schematic diagram illustrating a first variation of the water sampling system 100 illustrated in FIG. 1. In FIG. 1, the water sampling system 100 is illustrated as storing the sampled liquid in the water storage tank 20, but the water sampling system 100 is not limited to this. The water sampling system 100 may directly sample indicators of microbial load from the sampled liquid. For this purpose, the water sampling system 100 may have, instead of or in addition to the water storage tank 20, a filter 30 that collects microorganisms in the liquid sampled via the water sampling flow channel 102a based on control of the water sampling flow channel 102a by the controller 13 of the water sampling device 10.

The filter 30 may include, for example, a negatively charged membrane. The water sampling system 100 may perform microorganism sampling by capturing complexes with the negatively charged membrane included in the filter 30, where the complexes are formed by microorganisms in the liquid and cations added to the liquid.

Figure 5:
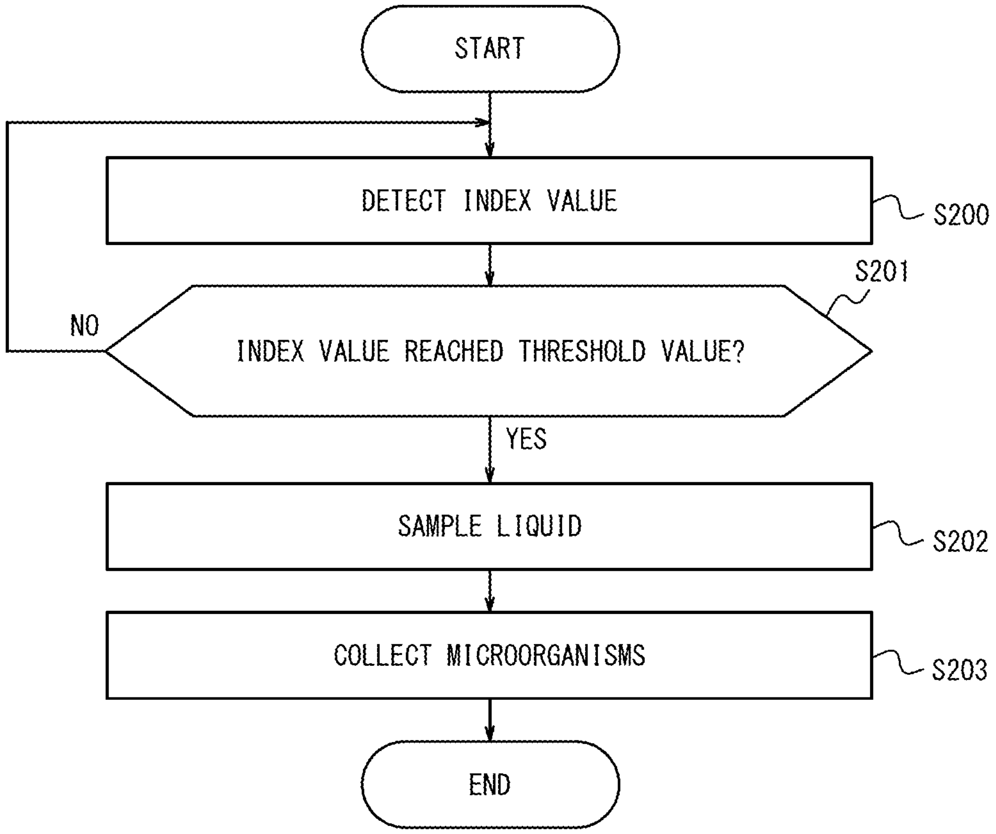
FIG. 5 is a flowchart for explaining a water sampling method executed by the water sampling system illustrated in FIG. 4.

FIG. 5 is a flowchart for explaining the water sampling method performed by the water sampling system 100 illustrated in FIG. 4. The water sampling method performed by the water sampling system 100 illustrated in FIG. 4 is described with reference to FIG. 5.

In step S200, the water sampling system 100 detects an index value related to the amount of microorganisms in the liquid flowing through the flow channel 102c.

In step S201, the water sampling system 100 determines whether the index value detected in the detection step of step 200 has reached the threshold value. Upon determining that the index value has reached the threshold value, the water sampling system 100 performs step S202. Upon determining that the index value has not reached the threshold value, the water sampling system 100 performs step S200 again.

In step S202, when the water sampling system 100 determines that the index value has reached the threshold value in the determination step of step S201, the liquid flowing in the flow channel 102c is sampled via the water sampling flow channel 102a as a liquid sample used to measure microorganisms. More specifically, the water sampling device 10 of the water sampling system 100 controls the water sampling flow channel 102a so that the liquid flowing in the flow channel 102c is sampled as a liquid sample used to measure microorganisms.

In step S203, the water sampling system 100 collects, by the filter 30, microorganisms in the liquid sampled in the water sampling step of step S202.

The method described above of directly collecting indicators of microbial load by the filter 30 allows for a more convenient evaluation of microbial load in the measurement of microorganisms at a later stage.

Figure 6:
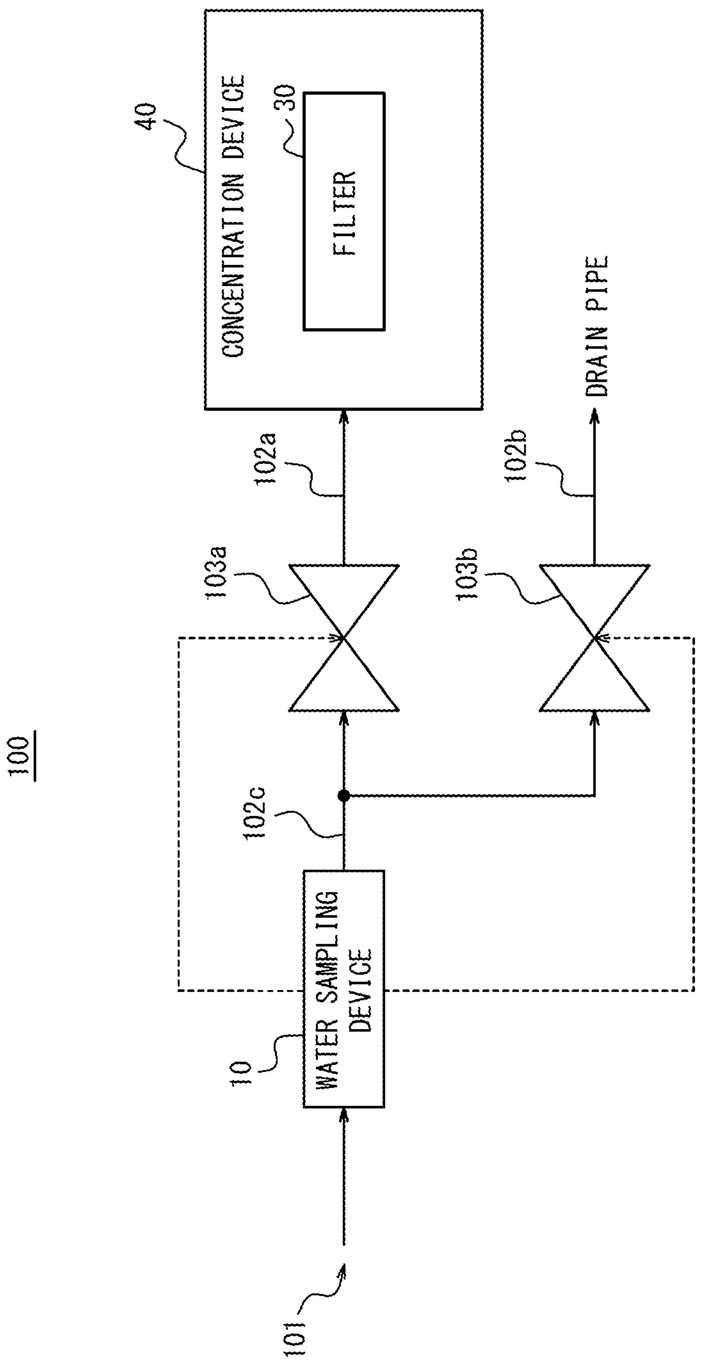
FIG. 6 is a schematic diagram illustrating a second variation of the water sampling system illustrated in FIG. 1.

FIG. 6 is a schematic diagram illustrating a second variation of the water sampling system 100 illustrated in FIG. 1. The water sampling system 100 may collect microorganisms that are indicators of microbial load collected by the filter 30 illustrated in FIG. 4 in a concentrated form. The water sampling system 100 may have a concentration device 40 that includes the filter 30.

The concentration device 40 may be configured based on any equipment that includes the filter 30. The concentration device 40, for example, concentrates microorganisms in the liquid that flows through the water sampling flow channel 102*a* to purify a concentrate. For example, the concentration device 40 concentrates the microorganisms collected by the filter 30 to purify the concentrate.

Figure 7:
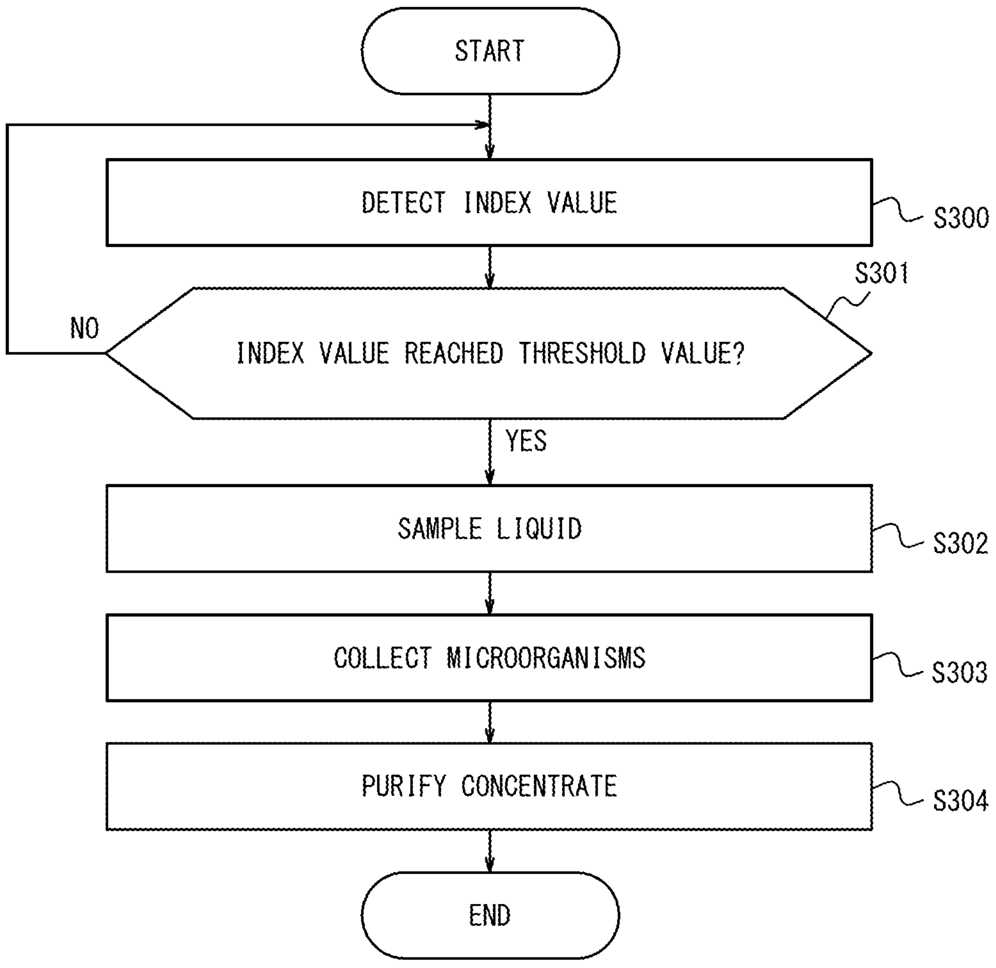
FIG. 7 is a flowchart for explaining a water sampling method executed by the water sampling system illustrated in FIG. 6.

FIG. 7 is a flowchart for explaining the water sampling method performed by the water sampling system 100 illustrated in FIG. 6. The water sampling method performed by the water sampling system 100 illustrated in FIG. 6 is described with reference to FIG. 7.

In step S300, the water sampling system 100 detects an index value related to the amount of microorganisms in the liquid flowing through the flow channel 102*c*.

In step S301, the water sampling system 100 determines whether the index value detected in the detection step of step 300 has reached the threshold value. Upon determining that the index value has reached the threshold value, the water sampling system 100 performs step S302. Upon determining that the index value has not reached the threshold value, the water sampling system 100 performs step S300 again.

In step S302, when the water sampling system 100 determines that the index value has reached the threshold value in the determination step of step S301, the liquid flowing in the flow channel 102*c* is sampled via the water sampling flow channel 102*a* as a liquid sample used to measure microorganisms. More specifically, the water sampling device 10 of the water sampling system 100 controls the water sampling flow channel 102*a* so that the liquid flowing in the flow channel 102*c* is sampled as a liquid sample used to measure microorganisms.

In step S303, the water sampling system 100 collects, by the filter 30, microorganisms in the liquid sampled in the water sampling step of step S302.

In step S304, the water sampling system 100 concentrates the microorganisms collected by the filter 30 in the collection step of step S303 to purify a concentrate.

As described above, the water sampling system 100 is able to directly collect a microbial load indicator by the filter 30 to concentrate the microorganisms. Therefore, the water sampling system 100 may use even a liquid sample that would be below a detection limit before concentration as a liquid sample that is possible to evaluate in subsequent microorganism measurement.

According to the first embodiment described above, when the index value does not reach the threshold value, the liquid that flows into the water sampling system 100 from the water sampling port 101 flows through the drainage flow channel 102*b* and is directed to the drain pipe, but the water sampling system 100 is not limited to this. The water sampling system 100 may have at least one of a water storage tank and a filter on a flow side where the second solenoid valve 103*b* is disposed.

Second Embodiment

Figure 8:
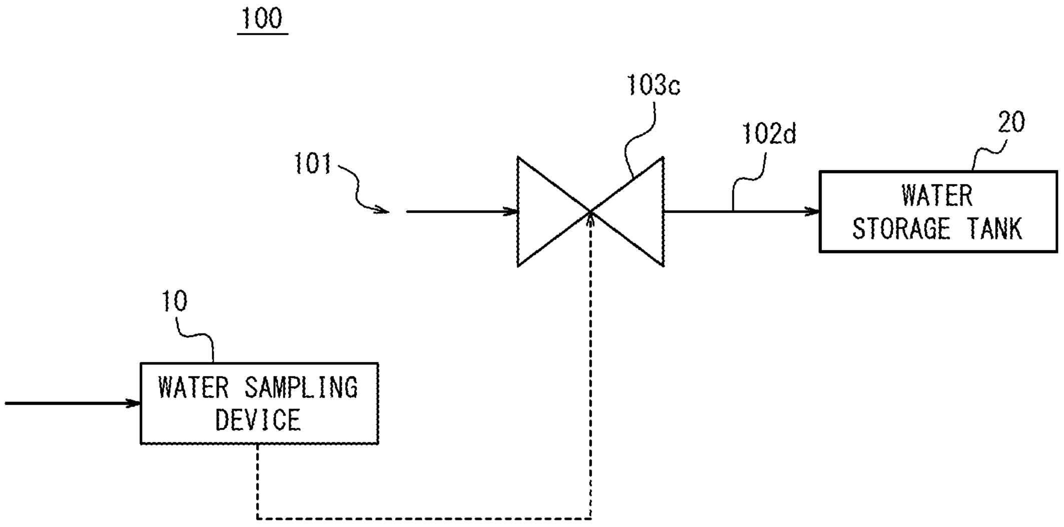
FIG. 8 is a schematic diagram of a water sampling system according to a second embodiment of the present disclosure.

FIG. 8 is a schematic diagram of the water sampling system 100 according to a second embodiment of the present disclosure. Configuration and functions of the water sampling system 100 according to the second embodiment are described with reference to FIG. 8. In FIG. 8, solid arrows connecting components indicate liquid flow. A dashed arrow starting from the water sampling device 10 indicates flow of signals.

The water sampling system 100 according to the second embodiment differs from the first embodiment in that the sensor 11 is disposed upstream of the water treatment process in the water treatment infrastructure rather than downstream of the water sampling port 101. Other configurations, functions, effects, variations, and the like are the same as in first embodiment, and the corresponding descriptions also apply to the water sampling system 100 according to the second embodiment. In the following, the same symbols are used for the same components as in the first embodiment, and descriptions thereof are not repeated. The main points that differ from the first embodiment are explained below.

The sensor 11 may detect an index value related to the amount of microorganisms in the liquid flowing in a flow channel further upstream of the water treatment process in the water treatment infrastructure than the water sampling port 101. The sensor 11 may be installed directly at a water flow point or other location in the water treatment infrastructure. For example, the detection point used in the detection step by the water sampling system 100 may be disposed at a most upstream point of the water treatment process in the water treatment infrastructure. On the other hand, the water sampling port 101 may be disposed to sample liquid as a liquid sample used to measure microorganisms for each downstream water treatment process in the water treatment infrastructure.

For example, referring to FIG. 8, the solenoid valve 103*c* is closed in advance. Upon obtaining an output signal from the calculator 12 regarding a determination result that the calculator 12 has determined that the index value has not reached the threshold value, the controller 13 maintains the solenoid valve 103*c* in the closed state. In this state, upon obtaining an output signal from the calculator 12 regarding a determination result that the calculator 12 has determined that the index value has reached the threshold value, the controller 13 outputs a control signal to the solenoid valve 103*c* to open the solenoid valve 103*c*. Accordingly, the solenoid valve 103*c* transitions from closed to open. At this time, the water storage tank 20 stores the liquid sampled via the water sampling flow channel 102*d* based on the control of the water sampling flow channel 102*d* by the controller 13.

Although the present disclosure has been described based on the drawings and examples, it should be noted that a person skilled in the art may make variations and modifications based on the present disclosure. Therefore, it should be noted that such variations and modifications are included within the scope of the present disclosure. For example, functions and the like included in each structure and step may be rearranged, and multiple structures and steps may be combined into one or divided, as long as no logical inconsistency results.

For example, the present disclosure may be realized as a program describing the processing content to realize each function of the water sampling system 100 described above, or as a storage medium on which the program is stored. The scope of the present disclosure should be understood to include these examples.

For example, the shape, arrangement, orientation, and number of each of the above components are not limited to those illustrated in the above description and drawings. The shape, arrangement, orientation, and number of each component may be configured arbitrarily, as long as the function thereof is achievable.

For example, the water sampling system 100 may perform only one of the water sampling methods described according to the first embodiment and the second embodiment above, or may perform the water sampling methods in combination with each other.

In the water sampling method according to an embodiment of the present disclosure, multiple detection points for the sensor 11 may be installed depending on the application, such as water treatment infrastructure. The water sampling method according to an embodiment of the present disclosure may be performed at a water sampling point before and/or after each water treatment process in water treatment infrastructure.

For example, based on the water sampling system 100 according to an embodiment described above, contamination and removal status may be ascertained based on the number of individual microorganisms present, regardless of whether the microorganisms are alive or dead.

For example, the water sampling system 100 according to an embodiment described above may have a pre-filter disposed upstream of the water storage tank 20 or the filter 30. Such a pre-filter may include any filter that has a pore size larger than a target microorganism and does not cause adsorption or the like of microorganisms.

In the water sampling system 100, a sampling time of liquid may be varied to allow for applications in the various fields mentioned above, including water supply, food, drinking water, and the like. In the water sampling system 100, the amount of water sampled may be set according to the microbial load. The shape of the water sampling port used as the water sampling port 101 for water sampling may be variable, and a removable water sampling port may be employed.

The invention claimed is:

1. A water sampling method comprising:
- detecting a plurality of index values related to an amount of microorganisms in a liquid flowing through a flow channel;
- calculating, for each of the plurality of index values obtained during operation of a system, a correlation between microbial load and the index value;
- selecting, from among the plurality of index values obtained during operation of the system, an index value having the highest correlation with the microbial load;
- setting the selected index value as a threshold value;
- detecting a current index value in the liquid flowing through the flow channel;
- determining whether the current index value has reached the threshold value; and
- when determining that the current index value has reached the threshold value, sampling via a water sampling flow channel the liquid flowing through the flow channel as a liquid sample to be used for measurement of the microorganisms.

2. The water sampling method according to claim 1, further comprising a water storage step of storing the liquid sampled in the water sampling step in a water storage tank.

3. The water sampling method according to claim 1, further comprising a collection step of collecting, by a filter, the microorganisms in the liquid sampled in the sampling step.

4. The water sampling method according to claim 3, further comprising a concentration step of concentrating the microorganisms collected by the filter in the collection step to purify a concentrate.

5. The water sampling method according to claim 1, the index value includes at least one of flow cytometer particles, turbidity, chromaticity, chemical oxygen demand (COD), biochemical oxygen demand (BOD), total organic carbon (TOC), dissolved oxygen (DO), suspended solids (SS), chlorophyll concentration, total nitrogen (T-N), total phosphorus (T-P), organic pollutant concentration (UV absorption analysis), adenosine triphosphate (ATP), or enzyme activity.

6. A water sampling device comprising:
- a sensor configured to detect a plurality of index values related to an amount of microorganisms in a liquid flowing through a flow channel;
- a calculator configured to calculate, for each of the plurality of index values obtained during operation of a system, a correlation between microbial load and the index value;
- a selector configured to select, from among the plurality of index values obtained during operation of the system, an index value having the highest correlation with the microbial load;
- a setter configured to set the selected index value as a threshold value,
- wherein the sensor is further configured to detect a current index value in the liquid flowing through the flow channel,
- wherein the calculator is further configured to determine whether the current index value detected by the sensor has reached a threshold value; and
- a controller configured to, when the calculator determines that the current index value has reached the threshold value, control a water sampling flow channel so that the liquid flowing through the flow channel is sampled as a liquid sample to be used for measurement of the microorganisms.

7. The water sampling device according to claim 6, the index value includes at least one of flow cytometer particles, turbidity, chromaticity, chemical oxygen demand (COD), biochemical oxygen demand (BOD), total organic carbon (TOC), dissolved oxygen (DO), suspended solids (SS), chlorophyll concentration, total nitrogen (T-N), total phosphorus (T-P), organic pollutant concentration (UV absorption analysis), adenosine triphosphate (ATP), or enzyme activity.

8. A water sampling system comprising:
- the water sampling device according to claim 6; and
- the water sampling flow channel through which the liquid to be sampled as the liquid sample flows.

9. The water sampling system according to claim 8, further comprising a water storage tank configured to store the liquid sampled based on the control of the water sampling flow channel by the controller.

10. The water sampling system according to claim 8, further comprising a filter configured to collect the microorganisms in the liquid sampled based on the control of the water sampling flow channel by the controller.

11. The water sampling system according to claim 10, further comprising a concentration device configured to concentrate the microorganisms collected by the filter to purify a concentrate.

* * * * *